(12) United States Patent
Federspiel et al.

(10) Patent No.: US 11,181,289 B2
(45) Date of Patent: Nov. 23, 2021

(54) SYSTEM AND METHOD FOR CONTROLLING THE HEATING, VENTILATION, AND AIR CONDITIONING (HVAC) IN A BUILDING TO DEFEND AGAINST PATHOGENS

(71) Applicant: Vigilent Corporation, Oakland, CA (US)

(72) Inventors: Clifford Conrad Federspiel, El Cerrito, CA (US); Peter Christian Varadi, El Cerrito, CA (US); Robert W. Thronson, San Mateo, CA (US); Benjamin Casey, Tracy, CA (US); James Patrick Rynne, Lafayette, CA (US); Cedric J. Clotilde, Hayward, CA (US)

(73) Assignee: Vigilent Corporation, Oakland, CA (US)

( * ) Notice: Subject to any disclaimer, the term of this patent is extended or adjusted under 35 U.S.C. 154(b) by 0 days.

(21) Appl. No.: 17/147,958

(22) Filed: Jan. 13, 2021

(65) Prior Publication Data

US 2021/0318010 A1    Oct. 14, 2021

Related U.S. Application Data

(60) Provisional application No. 63/009,577, filed on Apr. 14, 2020.

(51) Int. Cl.
*F24F 11/30* (2018.01)
*F24F 8/00* (2021.01)
(Continued)

(52) U.S. Cl.
CPC ............... *F24F 11/30* (2018.01); *F24F 3/16* (2013.01); *F24F 8/00* (2021.01); *F24F 11/64* (2018.01);
(Continued)

(58) Field of Classification Search
CPC .. F24F 11/30; F24F 11/64; F24F 11/72; F24F 11/80; F24F 8/00; F24F 3/16;
(Continued)

(56) References Cited

U.S. PATENT DOCUMENTS

2009/0126382 A1*   5/2009   Rubino ................... F24F 8/192
                                                              62/259.1
2016/0109149 A1    4/2016   Heller
(Continued)

FOREIGN PATENT DOCUMENTS

WO    WO-2019142599 A1 *   7/2019   .............. F24F 11/80

OTHER PUBLICATIONS

Cubick, Robert, "What is the Difference Between Latent and Sensible Loads in Radiant Cooling," Aug. 16, 2017, Uponor website (see next citation window for URL address) (Year: 2017).*

(Continued)

*Primary Examiner* — Marc E Norman
(74) *Attorney, Agent, or Firm* — Moser Taboada

(57) ABSTRACT

A computer implemented method and system for an automated customer service platform with human augmented conversational interleaving is disclosed. The method comprises estimating a latent load of the air in a zone being disinfected; selecting a set of one or more control from a plurality of control that is expected to improve the optimization metric; optimizing a metric for the set of allowable control and changing the setpoints of the set of control when the optimized metric has converged.

22 Claims, 5 Drawing Sheets

(51) Int. Cl.
*F24F 3/16* (2021.01)
*F24F 11/64* (2018.01)
*F24F 11/72* (2018.01)
*F24F 11/80* (2018.01)
*G05B 15/02* (2006.01)
*F24F 110/10* (2018.01)
*F24F 110/12* (2018.01)
*F24F 110/20* (2018.01)
*F24F 110/50* (2018.01)
*F24F 120/12* (2018.01)
*F24F 140/50* (2018.01)

(52) U.S. Cl.
CPC .............. *F24F 11/72* (2018.01); *F24F 11/80* (2018.01); *G05B 15/02* (2013.01); *F24F 2110/10* (2018.01); *F24F 2110/12* (2018.01); *F24F 2110/20* (2018.01); *F24F 2110/50* (2018.01); *F24F 2120/12* (2018.01); *F24F 2140/50* (2018.01); *F24F 2203/00* (2013.01)

(58) Field of Classification Search
CPC .. F24F 2110/10; F24F 3/12; F24F 3/20; F24F 3/50; F24F 2120/12; F24F 2140/50; G05B 15/02
See application file for complete search history.

(56) References Cited

U.S. PATENT DOCUMENTS

2018/0357577 A1* 12/2018 ElBsat .................. G06Q 10/04
2019/0091360 A1* 3/2019 Markesbery ............ A61L 2/183
2020/0348038 A1* 11/2020 Risbeck .................. F24F 8/10

OTHER PUBLICATIONS https://web.uponor.hk/radiant-cooling-blog/what-is-the-difference-between-latent-and-sensible-loads-in-radiant-cooling/#:~:text=Regarding%20HVAC%2C%20latent%20energy%20essentially,the%20relative%20humidity%20was%20high.&text=The%20warmer%20air%20is%2C%20the,to%20as%20the%20relative%20humidity. (Year: 2017).*
International Search Report and Written Opinion, dated Apr. 27, 2021 for International Application No. PCT/US2021/013224.

* cited by examiner

SYSTEM AND METHOD FOR CONTROLLING THE HEATING, VENTILATION, AND AIR CONDITIONING (HVAC) IN A BUILDING TO DEFEND AGAINST PATHOGENS

CROSS-REFERENCE TO RELATED APPLICATIONS

This application claims priority to U.S. Provisional Patent Application Ser. No. 63/009,577 filed Apr. 14, 2020, which is incorporated by reference herein in its entirety.

FIELD

Embodiments of the present invention generally relate to inactivating pathogens and, more particularly, to a system and method for controlling the HVAC in a building to defend against pathogens.

BACKGROUND

During a pandemic, many organizations require employees to continue to work in offices, factories, and stores. However, viruses are easily transmitted in the air and on surfaces within the workplace. The transmission and spread of viruses are largely dependent on temperature and humidity. Most aerosol viruses are inactivated more slowly (i.e., are more stable) when temperature and humidity are low and are inactivated faster when temperature is high or humidity is moderate. However, in some cases, aerosol viruses are more stable at very high humidity, close to 100%. Viruses can also be transmitted via contact with contaminated surfaces and may be more stable on surfaces than in aerosols.

The effects of humidity as related to pathogen response include physiological effects, physical effects, and chemical effects. Lower humidity increases the viscosity of mucous in the respiratory tract and also impairs the immune system response to infection. This has the effect of changing the dose-response of the pathogen. At lower humidity, a lesser pathogen exposure may yield the same probability of infection as a greater pathogen exposure at higher humidity.

Pathogen-loaded droplets in aerosols that are discharged by infected hosts evaporate in air at low humidity. Evaporation reduces the sizes of the droplets, which extends the amount of time that the droplets can remain airborne and effects the trajectory of intermediate-sized droplets. Evaporation also increases the salinity of a droplet and reduces its pH. Both of these chemical changes to discharged pathogen-loaded droplets can cause viruses to become inactivated sooner than they would without these changes.

Currently, organizations are dealing with pathogens by requiring employees to wear masks and manually attempting to disinfect workplaces when employees are absent. This is both inefficient and ineffective.

Therefore, there is a need in the art for a system and method for controlling the HVAC in a building to defend against pathogens.

SUMMARY

A system and method for controlling the HVAC in a building to defend against pathogens substantially as shown in and/or described in connection with at least one of the figures, as set forth more completely below.

In some embodiments, a system for controlling an HVAC system in a building to defend against pathogens includes: an HVAC system; a building management system integrated with the HVAC system; and a pathogen defense system. In some embodiments, the pathogen defense system includes: a) at least one processor; b) at least one input device; and c) at least one storage device storing processor-executable program instructions which, when executed by the at least one processor, perform methods as described in any of the embodiments disclosed herein. In some embodiments, the method includes: estimating a latent load of air in a zone being disinfected; selecting a set of one or more control variables from a plurality of control variables that is expected to improve an optimization metric; optimizing a metric for the set of control variables; and changing a setpoint of each control variable in the set of control variables when the optimized metric has converged.

These and other features and advantages of the present disclosure may be appreciated from a review of the following detailed description of the present disclosure, along with the accompanying figures in which like reference numerals refer to like parts throughout.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

Figure 1:
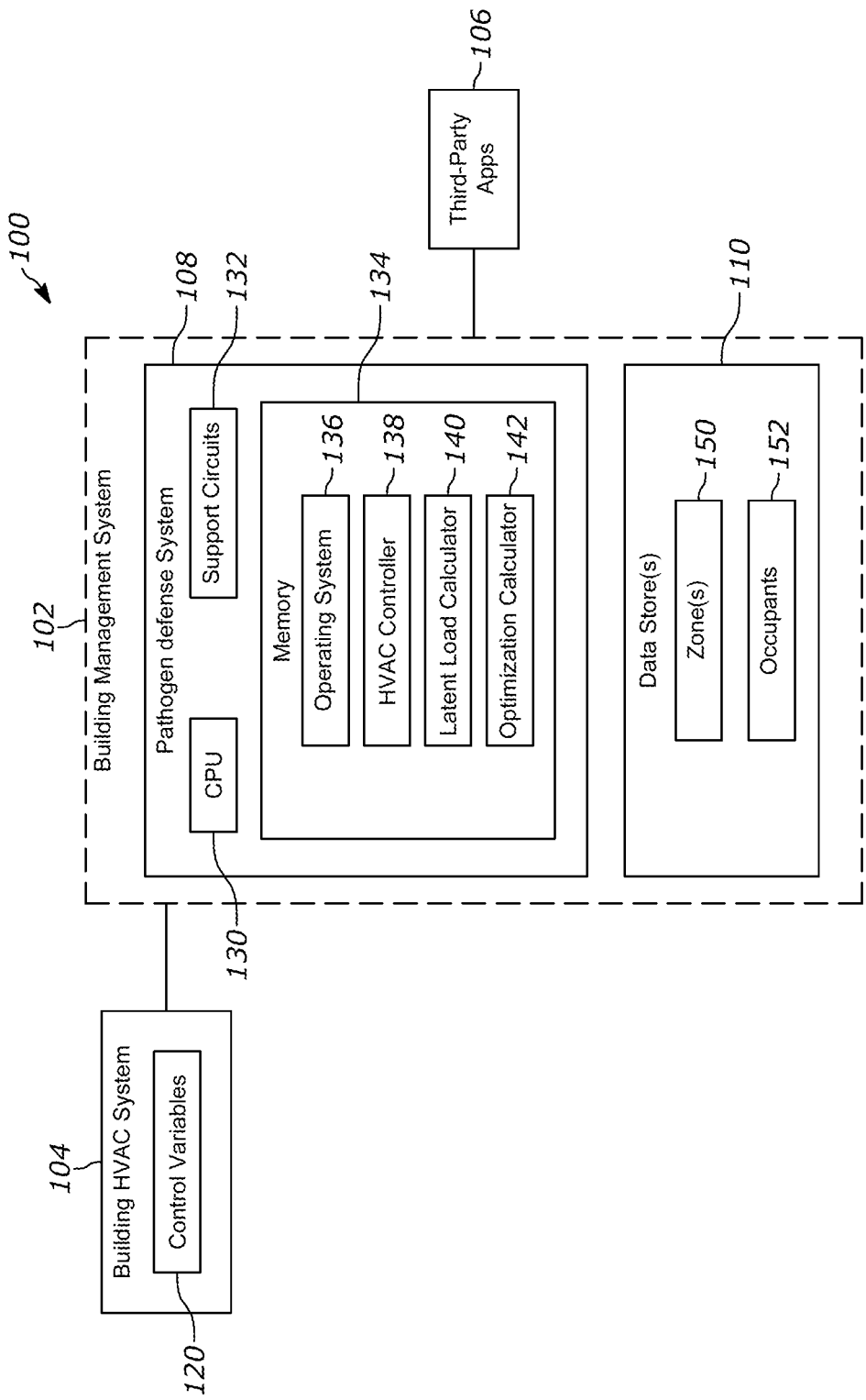
FIG. 1 depicts a block diagram of a system for controlling the HVAC in a building to defend against pathogens, in accordance with exemplary embodiments of the present invention.

While the system and method are described herein by way of example for controlling the HVAC in a building to defend against pathogens, those skilled in the art will recognize that the system and method for controlling the HVAC in a building to defend against pathogens is not limited to the embodiments or drawings described. It should be understood, that the drawings and detailed description thereto are not intended to limit embodiments to the particular form disclosed. Any headings used herein are for organizational purposes only and are not meant to limit the scope of the description or the claims. As used herein, the word "may" is used in a permissive sense (i.e., meaning having the potential to). Similarly, the words "include", "including", and "includes" mean including, but not limited to.

DETAILED DESCRIPTION

Embodiments of the present invention generally relate to controlling the HVAC in a building to defend against pathogens. Based on factors regarding the transportation of a specific contaminant, a building management system adjusts the setpoints of a building HVAC system, including for example a supply duct static pressure setpoint, a supply air temperature setpoint, a supply airflow setpoint of unitary equipment or variable air volume (VAV) terminal units, a chilled water differential pressure setpoint, a chilled water temperature setpoint, and the like, to efficiently and effectively inactivate a pathogen.

Various embodiments of a system and method for controlling the HVAC in a building to defend against pathogens are described. In the following detailed description, numerous specific details are set forth to provide a thorough understanding of claimed subject matter. However, it will be understood by those skilled in the art that claimed subject matter may be practiced without these specific details. In other instances, methods, apparatuses or systems that would be known by one of ordinary skill have not been described in detail so as not to obscure claimed subject matter.

The transportation of a contaminant in a building is affected by a number of factors, such as the accumulation of a contaminant in indoor air spaces, a concentration of the contaminant in the outdoor air drawn into the building for ventilation or cooling, an air exchange between different regions or zones of a building, air movement within a region or zone of a building, and the like. Where contaminants are infectious pathogens, the outdoor air entering the building is not likely to be contaminated. However, the concentration of a pathogen in indoor air is affected by filtration of the pathogen, and by a settling of particles containing the pathogen. The concentration of infectious pathogens is also affected by the inactivation rate (i.e., death rate) of the pathogen.

In the zonal model of contaminant transport in buildings, the air within a zone is assumed to be perfectly mixed. The simplest zonal model is a single-zone model. The dilution, removal, and inactivation dynamics for a single-zone model include the accumulation of a contaminant such as a pathogen, the inflow of the contaminant from outside the zone via ventilation, the removal of the contaminant via ventilation, the capture of the contaminant by filtration, the settling of particles containing the pathogen, and the inactivation of pathogens, plus the emission rate within the zone by someone who is infected. Mathematically, these terms are part of the following equation:

$$V\dot{C}_a = F_s(1-\Phi)(1-\eta)C_a - F_sC_a - kVC_a - \frac{v}{H}VC_a + E \quad (1a)$$

where V is the volume of the indoor air inside the fixed-boundary zone, $C_a$ is the concentration of contaminant (e.g., infectious pathogen) in the indoor air, $F_s$ is the supply airflow rate, $\Phi$ is the fraction of outdoor air in the supply air, $\eta$ is the filtration efficiency, k is the inactivation rate of the pathogen, v is the settling velocity of particles containing the pathogen, H is the height of the indoor space, and E is the pathogen source emission rate. The supply airflow rate and the fraction of outdoor air in the supply air can be measured. The inactivation rate can be determined from DHS models. The settling velocity is calculated based on relative humidity.

The inactivation rate is dependent on the indoor temperature, the indoor humidity, and the presence and operation of ultraviolet lamps, ionization devices, and other devices that inactivate pathogens. The United States Department of Homeland Security (DHS) has developed a model relating the half-life of the SARS-Cov-2 virus to temperature, relative humidity, and UV index. There is a one-to-one relationship between half-life and inactivation rate.

The settling rate is dependent on indoor relative humidity because the relative humidity affects the equilibrium particle size of droplets expelled by infected hosts. The settling rate can be computed using Kohler theory to first determine the equilibrium particle size, and then compute the terminal velocity of a particle. The equation for surface accumulation is as follows:

$$\dot{N}_s = -k_sN_s + \frac{v}{H}VC_a \quad (1b)$$

where $N_s$ is the number of pathogens on surfaces and $k_s$ is the surface inactivation rate, which can be determined from the DHS surface model.

The pathogen loss rate, R is as follows:

$$R = \frac{F_s}{V}[1-(1-\Phi)(1-\eta)] + k + \frac{v}{H} \quad (2)$$

For a fixed value of R the fractional concentration (relative to the initial concentration) of infectious pathogen remaining at time duration t after a quantity of pathogens has been expelled into the indoor air is as follows:

$$f = e^{-Rt} \quad (3)$$

The larger the value of the pathogen loss rate R, the faster that the fractional concentration decreases. If there is no pathogen emission, such as is the case for after-hours operation, then the fraction of surface pathogens can be estimated or determined from Equation 1a.

Assuming that the concentration of a pathogen in the outdoor air is zero and that the pathogen is released into the indoor air at a steady rate, the steady-state concentration of a pathogen indoors is as follows:

$$C_{a,ss} = \frac{E_{ss}}{R} \quad (4)$$

Therefore, the larger the value of pathogen loss rate R, the smaller the value of the steady-state pathogen concentration.

The probability of infection or the expected fraction of a population that will become infected is greater at higher concentrations, which corresponds to a higher release of pathogens. Such a relationship is called a dose-response curve and is modeled as a function of exposure, where for a respiratory pathogen exposure is the quantity of pathogens inhaled over a period of time. An exponential distribution is the most common dose-response curve for respiratory viral infection.

$$P = 1 - e^{-\frac{ln(2)D}{ID50(w,T)}} \quad (5)$$

where $ID_{50}(w,T)$ is the dose of pathogen that will result in 50% of the population becoming infected at a condition of temperature and humidity (e.g., 22° C. and 50% relative humidity).

Low humidity generally results in a lower infectious dose.

The dose, D, is the product of the breathing rate b (e.g., liters per minute), lung deposition fraction d, and the concentration of pathogens in the breathing zone, $C_a$, and the duration of the exposure T (minutes). At steady-state, the dose is as follows:

$$D = b d C_{a,ss} T \quad (6)$$

If the exposure is not at steady-state, then Equation 1a must be integrated over the exposure duration to determine the dose.

Equations 5 and 6 are equivalent to the Wells-Riley model of infection where ID50/ln(2) is one quantum (the amount of infectious pathogen that results in 63% probability of infection) and $C_a$ is the concentration of quanta in the air.

Humidity is an important factor for pathogen inactivation and settling. When the HVAC system cannot or is not actively humidifying, the humidity ratio can be modeled using the same approach as Equation 1a above. Although there is no filtration, inactivation, or settling, the term for removal by condensation at the cooling coil of an air-handling unit is represented in the equation:

$$\rho V \dot{w}_a = -\rho F_o(w_a - w_o) - \rho F_s(w_m - w_s) + L \quad (7)$$

where $\rho$ is the density of air, $w_a$ is the humidity mass ratio of indoor air, $F_o$ is the outdoor airflow rate, $w_o$ is the humidity mass ratio of outdoor air, $w_m$ is the humidity mass ratio of mixed air, $w_s$ is the humidity mass ratio of supply air, and L is the latent load.

Some portions of the detailed description that follow are presented in terms of algorithms or symbolic representations of operations on binary digital signals stored within a memory of a specific apparatus or special purpose computing device or platform. In the context of this particular specification, the term specific apparatus or the like includes a general-purpose computer once it is programmed to perform particular functions pursuant to instructions from program software. Algorithmic descriptions or symbolic representations are examples of techniques used by those of ordinary skill in the signal processing or related arts to convey the substance of their work to others skilled in the art. An algorithm is here, and is generally, considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these or similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a specific apparatus, such as a special purpose computer or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device.

FIG. 1 depicts a block diagram of a system 100 for controlling the HVAC in a building to defend against pathogens, in accordance with exemplary embodiments of the present invention. The system 100 comprises a building management system (BMS) 102, a building HVAC system 104, a plurality of third-party applications 106, and a pathogen defense system 108. The pathogen defense system 108 is integrated with the BMS 102 and a data store 110. The data stores 110 store information regarding each zone 150 in a building, such as dimensions of the zone, air volume, maximum temperature, comfort level, time occupants are to be present, and the like. The data stores 110 also store information regarding each occupant 152 in the building, including any health or infection readings taken for an occupant 152.

The building HVAC system 104 is integrated as part of a building and comprises at least a plurality of control variables 120 for various items in the HVAC system 104 that may be adjusted.

In some embodiments, the pathogen defense system 108 is located on-premises or in a computing environment that is within an organization's network and firewall protections. In some embodiments, the pathogen defense system 108 is located off-site in a cloud computing platform such as Amazon Web Services (AWS), Microsoft® Azure, or Google® Cloud. In some embodiments, the pathogen defense system 108 integrates with the BMS 102 using open protocols such as BACnet/IP or Modbus-TCP. In some embodiments, the pathogen defense system 108 is integrated using an application programming interface (API). In some embodiments, a cellular modem is used to connect a remote, cloud-based pathogen defense system 108 to the BMS 102 using a secure tunnel. In such embodiment, the secure tunnel is directly established between the remote, cloud-based pathogen defense system 108 and the BMS 102.

The pathogen defense system 108 integrates with third-party applications 106 to determine for example, weather conditions from a weather app, the current infection rate across a population from an informatics system, an extent a building is likely to be exposed to infected occupants, from a local government and/or health organization, and the like.

The pathogen defense system 108 may comprise a Central Processing Unit (CPU) 130, support circuits 132, and a memory 134. The CPU 130 may comprise one or more commercially available microprocessors or microcontrollers that facilitate data processing and storage. The various support circuits 132 facilitate the operation of the CPU 130 and include one or more clock circuits, power supplies, cache, input/output device and circuits, and the like. The memory 134 comprises at least one of Read Only Memory (ROM), Random Access Memory (RAM), disk drive storage, optical storage, removable storage and/or the like. In some embodiments, the memory 134 comprises an operating system 136, an HVAC controller 138, a latent load calculator 140, and an optimization calculator 142.

The operating system (OS) 136 generally manages various computer resources (e.g., network resources, file processors, and/or the like). The OS 136 is configured to execute operations on one or more hardware and/or software modules, such as Network Interface Cards (NICs), hard disks, virtualization layers, firewalls and/or the like. Examples of the OS 136 may include, but are not limited to, various versions of LINUX, MAC OSX, BSD, UNIX, MICROSOFT WINDOWS, IOS, ANDROID and the like.

The HVAC controller 138 adjusts control variables 120 of the building HVAC system 104. Control variables 120 may include the supply duct static pressure setpoint, the supply air temperature setpoint, the supply airflow setpoint of unitary equipment or variable air volume (VAV) terminal units, the chilled water differential pressure setpoint, the chilled water temperature setpoint, and the like.

The pathogen defense system 108 operates in one of a plurality of modes, specifically Green Mode, Health Mode, and Disinfect Mode. In each mode the pathogen defense system 108 uses the optimization calculator 142 to optimize a performance metric, using the latent load calculator 140 as described below. Metrics may include energy or power consumption, the pathogen loss rate, or the probability of infection.

In some cases, because of competing factors, maximizing the pathogen loss rate or minimizing probability of infection has multiple solutions, or a set of solutions where when the independent variables are changed, the result has only a small effect on the metric. Such optimization problems are called ill-posed. When the optimization problem is ill-posed, optimization is performed using regularization. Regularization can be achieved by incorporating energy consumption and either the pathogen loss rate or the probability of infection, rather than both, into a single metric to be optimized. In one embodiment, the specific choice of the metric may be made by a building operator or engineer. In another embodiment a user inputs information about their building (e.g., location, configuration, hours of operation, if humidity control exists, etc.) and the pathogen defense system 108 recommends when different modes (Green, Health, Disinfect) and different metrics should be used.

When the pathogen defense system 108 is operated in Green Mode, the building is operated to minimize the energy consumption of the building HVAC system 104 while maintaining comfort levels in multiple zones, each potentially with a different set of configured comfort levels. In one embodiment, for variable air volume (VAV) HVAC systems where one supply duct system feeds into multiple VAV boxes and each VAV box is typically associated with one zone, the duct static pressure setpoint and the supply air temperature setpoint may be adjusted to ensure that zone temperatures remain within configured or learned bounds, and these zone temperature bounds are achieved using a low level of total HVAC energy.

When the pathogen defense system 108 is operated in Health Mode, the building HVAC system 104 is operated to regulate or optimize a metric related to the presence or effect of an airborne contaminant such as a viral pathogen. In one embodiment, the metric for Health Mode may be the pathogen loss rate. In another embodiment, the metric for Health Mode may be the probability of infection. Since optimizing for pathogen loss rate or probability of infection may be ill-posed and may consume substantially more energy than Green Mode, maximizing a metric using the pathogen loss rate may be used to achieve a cost-effective decontamination. In some embodiments, minimizing a metric using the probability of infection may be used for the same purpose of regularization and cost-effectiveness. In some embodiments, the pathogen loss rate or probability of infection are regulated rather than optimized. The pathogen loss rate or probability of infection are regulated to use the least amount of power consumption while conforming to comfort constraints. Like Green Mode, Health Mode controls the HVAC system 104 to maintain zone temperatures within configured or learned upper and lower bounds for thermal comfort. In one embodiment, the configured upper bounds for zone temperatures are elevated during Health Mode to facilitate optimization of the selected metric at the possible expense of thermal comfort.

When humidification is available, it may be possible to find an operating point that minimizes energy consumption and optimizes the selected infection metric simultaneously. In other words, it may be possible to control the humidity so that the optimal settings of control variables 120 of the building HVAC system 104 (e.g., supply air temperature setpoint, supply duct static pressure setpoint, etc.) are the same for Green Mode and Health Mode. Therefore, in another embodiment, humidity is controlled to keep the operating point for Health Mode as close as possible to the operating point for Green Mode.

During warmer weather when the outdoor air cannot be used for cooling, the supply water temperature of a chiller plant is adjusted (in addition to the supply air temperature) so that condensation of water from the supply air results in an indoor humidity that optimizes the selected metric. As such, in another embodiment, the chilled water temperature setpoint is adjusted to control air humidity in a manner that optimizes the selected optimization metric.

When the pathogen defense system 108 is operated in Disinfect Mode, the building HVAC system 104 is operated at a high temperature for an extended period of time to not only inactivate airborne pathogens, but also inactivate pathogens on surfaces. If the humidity can also be elevated, then the building HVAC system 104 is operated at high temperature and higher humidity. In some embodiments, a high-temperature operation is invoked by changing the zone temperature setpoint of zones to be disinfected, which causes the HVAC controller 138 to increase temperatures in the associated areas accordingly. In another embodiment, high-temperature operation is invoked utilizing any available reheating capability of the building HVAC system 104, e.g., via hot water or electric reheat at the VAV boxes, by overriding the (re)-heating valves to a fully open position, by increasing current to the reheating coils, by increasing airflow setpoints of VAV boxes with reheat, or by fully opening dampers of VAV boxes with reheat. In another embodiment, high-temperature operation is invoked by sending the BMS 102 a command to switch to and use a configuration that will cause the building to heat up.

Since viruses such as SARS-Cov-2 have been shown to be very stable on surfaces, the building temperature is raised to levels that are higher than would normally be acceptable for comfort (e.g., 35° C.). When the outdoor air is hotter than the indoor air, Disinfect Mode may use the hot outdoor air to warm the building. This also causes contaminated indoor air to be flushed from the building. Doing so can reduce the energy cost of Disinfect Mode. Disinfect Mode ends at a predetermined time prior to the occupants returning to the building, or after an optimization metric has reached a predetermined level. Disinfect Mode may involve a defined cool-down period that uses large amounts of outdoor air to cool the building back to regular comfort levels if the outdoor air is sufficiently cool and dry. This cool-down period, when enabled by cool and dry outdoor air, dilutes airborne pathogens further, which may be taken into account for determining operational parameters for the Disinfect Mode and the cool-down period. Disinfect Mode might be used overnight or on weekends in a single-shift commercial building such as an office building. For many buildings and HVAC systems, heating can be applied on a granular basis. As such, in some embodiments, Disinfect Mode is invoked on a granular level in a building, such as on a per-floor or per-zone basis. When these modes of operation are applied on a granular level, it may be advisable to interact with the building management system 102, or with the building management team, to keep zones physically isolated for the duration of a mode, for example by keeping doors closed to keep the zones contained.

In some embodiments, Disinfect Mode is operated long enough to reduce an estimated fraction of infectious virus to a target level. A model such as a Department of Homeland Security (DHS) surface model may be used to determine the estimated fraction and estimate the termination time. An optimization algorithm is used to drive the infectious virus fraction to the target in minimum time. This optimization includes driving the state of the building back to an operating condition that is acceptable for occupants as soon as possible or as efficiently as possible. Alternatively, control is returned to the HVAC controller in its normal mode of operation, which will attempt to reestablish the comfort temperatures bounds in the zones in terms of regular control.

In another embodiment, Disinfect Mode is operated with a fixed time horizon. At the end of the time horizon, the building must be back at an operating condition that is acceptable for occupants. Optimization is used to maximize the disinfection effect over the time horizon.

By optimizing a metric such as those described above, the performance of the control system can be reported. In some embodiments, energy use, the pathogen loss rate, and the probability of infection are reported for Health Mode. In another embodiment, energy use and the disinfect fraction (fraction of surface viruses remaining) are reported for Disinfect Mode. In a multi-zone building, it may not be possible to achieve the same optimal contaminant/pathogen reduction levels in all zones equally. The control system may report on the zones that have not achieved desired levels. These quantities and metrics can be reported even if Health Mode and Disinfect Mode are not used and provide an estimate of the missed opportunity if the decision is made, e.g. by human intervention into the control system, not to enable Health or Disinfect Modes. The pathogen defense system 108 typically runs in Green Mode until triggered to switch to Health Mode or Disinfect Mode.

Figure 2:
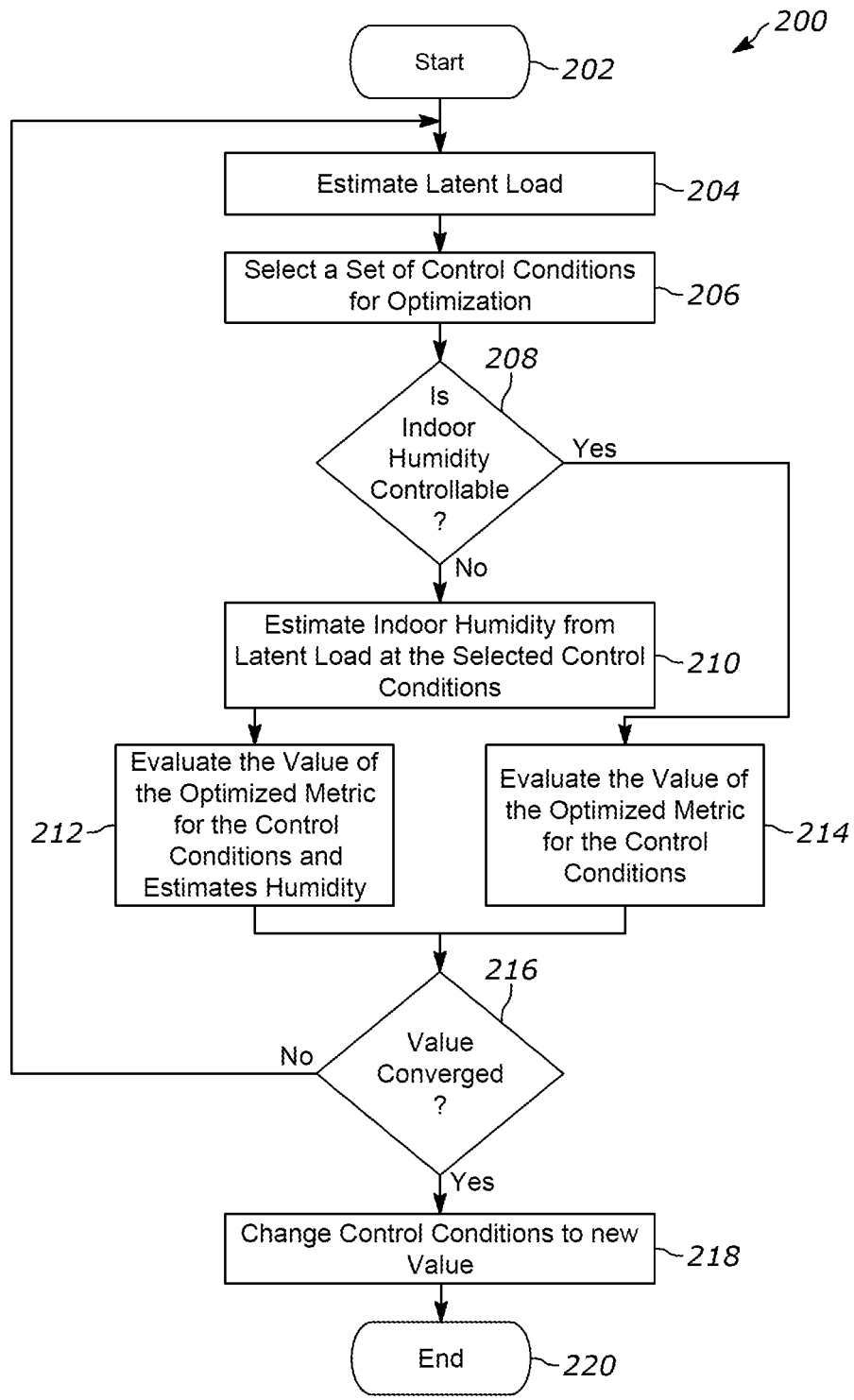
FIG. 2 depicts a flow diagram of a method for operating the pathogen defense system in Health Mode, in accordance with exemplary embodiments of the present invention.

FIG. 2 depicts a flow diagram of a method 200 for operating the pathogen defense system in Health Mode, in accordance with exemplary embodiments of the present invention. The method 200 may be triggered by an informatics system, such as Kinsa® or CovidActNow or the data store at Johns Hopkins University indicating that a health metric, such as a percent of the local population with fever or infection has crossed a level that indicates that some building occupants may be infected with a pathogen. The method 200 starts at step 202 and proceeds to step 204.

At step 204, an estimated latent load is calculated. The latent load can be estimated using the following equation:

$$\rho V \dot{w}_a = \rho F_o(w_o - w_a) + L \quad (8a)$$

The derivative of an indoor humidity ratio is estimated with a finite difference using the following equation:

$$\hat{L} = \rho V \frac{w_a(t) - w_a(t-\tau)}{\tau} + \rho F_o \frac{w_a(t) + w_a(t-\tau) - w_o(t) - w_o(t-\tau)}{2} \quad (8b)$$

The latent load includes evaporation of water from building occupants, devices that use water, such as coffee makers, and the like. The latent load may also include mass transfer with building materials. The estimate in Equation 8b can be smoothed with a low-pass filter to reduce the effects of noise introduced by approximating the derivative by a finite difference. The humidity ratio (w) is determined from relative humidity and temperature. Indoor values of relative humidity and temperature are determined by the BMS. Outdoor values may be determined from a BMS or an internet weather station/service. Flow rates are determined by a BMS.

At step 206, a set of one or more control variables is selected for optimizing a metric. A metric may be one or more of energy or power consumption, pathogen loss rate, or the probability of infection. Control variables may include the supply airflow rate, the outdoor airflow rate, the indoor temperature, or the like). The starting values for the control variables are typically their present values for the gradient/Newton search approach. The control variables that are available depends on the design of the HVAC system. For example, in a system with variable air volume (VAV) units, supply airflow setpoints are adjustable. In other systems supply airflow is not a control variable, but humidity is controllable.

At step 208, it is determined whether the indoor humidity is controllable. If at step 208, it is determined that the indoor humidity is controllable, then the method proceeds to step 214, where the value of the metric being optimized is evaluated for the control variables. However, if at step 208, it is determined that the indoor humidity rate is not controllable, then at step 210, the indoor humidity is estimated from the estimated latent load at the selected control variables. The future indoor humidity ratio is computed as follows:

$$\hat{w}_{a,ss} = \frac{\hat{L}}{\rho \overline{F}_o} + w_o$$

This is the steady-state (equilibrium) value that would result if the outdoor airflow rate were set to a value of $\overline{F}_o$.

At step 212, the value of the metric being regulated or optimized is evaluated for the control and the estimated humidity.

At step 216, it is determined whether the values of the optimized metric converge for the set of control variables. Values converge when the changes from the optimization values are smaller than a predefined threshold. If the values do not converge, then the method proceeds to step 206 where a different set of control variables is selected for optimization, and the method iterates until at step 216, the values converge and the method proceeds to step 218.

At step 218, the setpoints for the control are changed to the new value. In some embodiments, the setpoints are displayed such that the control variables can be modified manually.

The method 200 ends at step 220.

Figure 3:
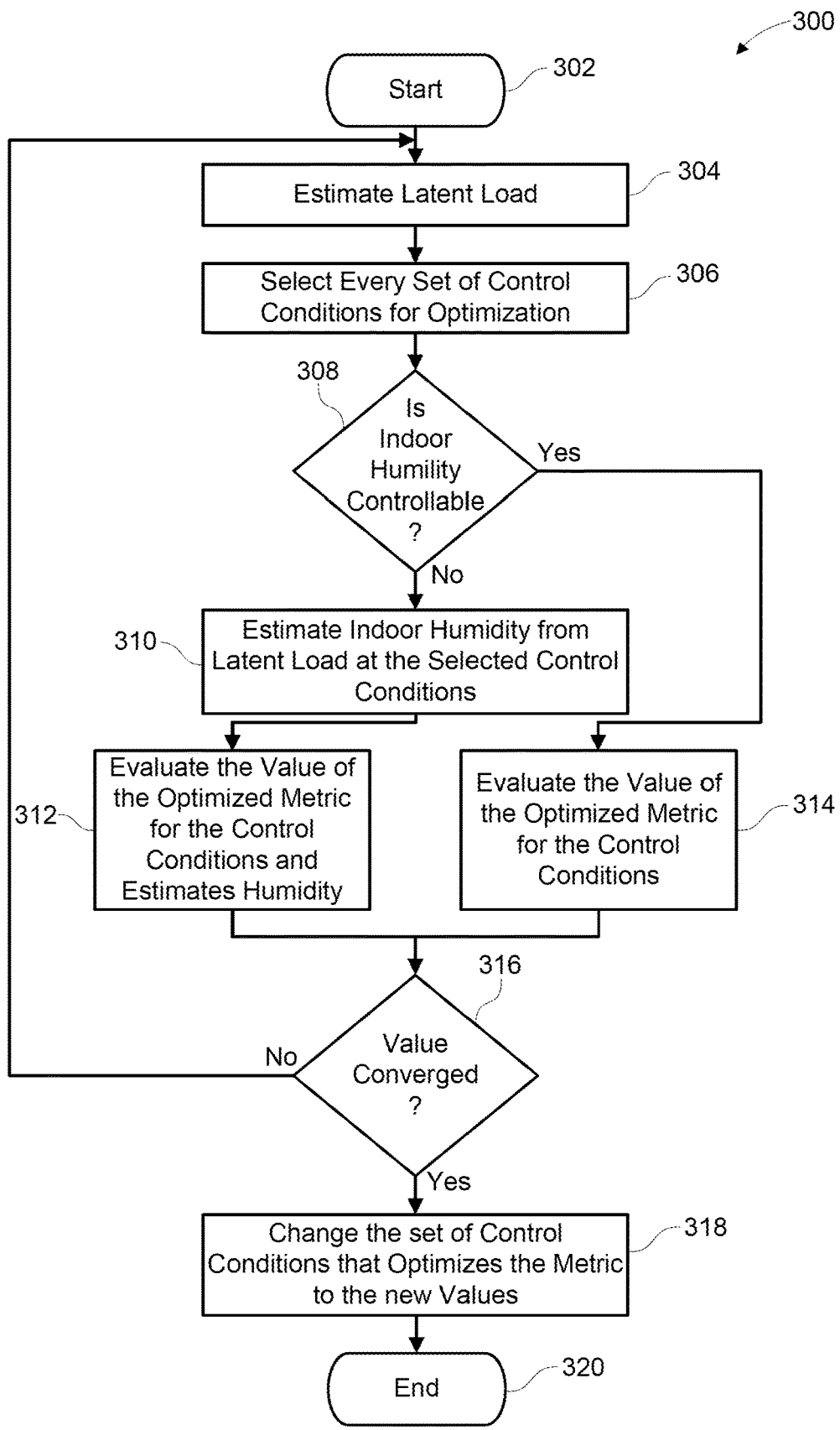
FIG. 3 depicts a flow diagram of a method for operating the pathogen defense system in Health Mode, in accordance with exemplary embodiments of the present invention

FIG. 3 depicts a flow diagram of a method 300 for operating the pathogen defense system in Health Mode, in accordance with exemplary embodiments of the present invention. In some embodiments, the method 300 may be triggered by a notification that someone in the building has been in contact with an infected person. In some embodiments, the method 300 is triggered when a notification from an informatics system indicates a health metric such as a percent of the local population with a fever or infection has crossed a predefined level. The method 300 starts at step 302 and proceeds to step 304.

At step 304, an estimated latent load is calculated. As described above in step 204.

At step 306, all sets of control variables are selected for optimizing a metric.

At step 308, it is determined whether the indoor humidity is controllable. If at step 308, it is determined that the indoor humidity is controllable, then the method proceeds to step 314, where the value of the metric being optimized is evaluated for the control variables. However, if at step 308, it is determined that the indoor humidity rate is not controllable, then at step 310, the indoor humidity is estimated from the latent load at the selected control variables.

At step 312, the value of the metric being optimized is evaluated for the control variables and the estimated humidity.

At step 316, it is determined whether the values of the optimized metric converge for the set of control variables. If the values do not converge, then the method proceeds to step 306 where a different set of control variables is selected for optimization, and the method iterates until at step 316, the values converge and the method proceeds to step 318.

At step 318, the setpoints of the control variables that optimized the metric are changed to the new value.

The method 300 ends at step 320.

Figure 4:
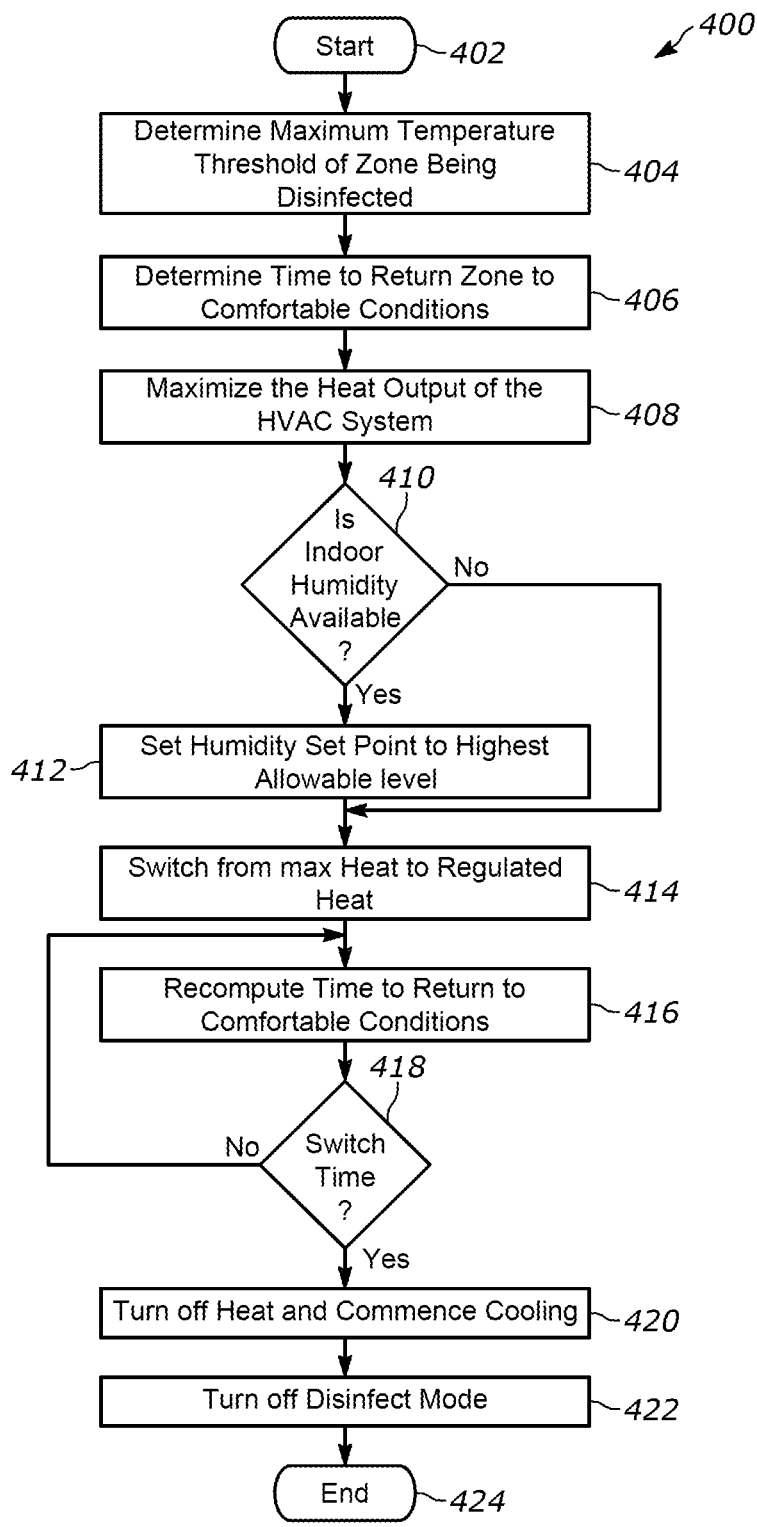
FIG. 4 depicts a flow diagram of a method for operating the pathogen defense system in Disinfect Mode, in accordance with exemplary embodiments of the present invention.

FIG. 4 depicts a flow diagram of a method 400 for operating the pathogen defense system in Disinfect Mode, in accordance with exemplary embodiments of the present invention. The method 400 may be triggered overnight or over a weekend after a notification has been received that a percent of a local population infected by a pathogen has crossed a predefined level. In another embodiment, Disinfect Mode may be triggered when the pathogen defense system is in Health Mode and all occupants have left a workplace. The method 400 is performed for each zone that is being disinfected. The method 400 starts at step 402 and proceeds to step 404.

At step 404, the maximum temperature threshold for the zone is determined. Each zone may have a different maximum temperature threshold. The data stores of the building management system are accessed to determine the maximum temperature threshold for the zone being disinfected.

At step 406, the amount of time that the zone needs to switch out of Disinfect Mode so that the workplace can be returned to comfortable conditions for occupancy is determined. The disinfection process must cease and a cooling process must be completed before occupants return to the workplace. The time that occupants are to return to the zone is retrieved from the data stores of the building management system. The time to cease Disinfect Mode is calculated from the retrieved time. For example, if occupants are expected to return to the building at 7 am, and the cooling process takes 1.5 hours, the time to switch to the cooling phase of Disinfect Mode is 5:30 am.

At step 408, the heat setpoint is set to the maximum heat output of the HVAC system.

At step 410, it is determined whether indoor humidity is a controllable parameter. If the indoor humidity can be controlled, then at step 412, the humidity setpoint is set to the highest allowable level. In some embodiments, the outdoor air is assessed to determine if the outdoor air is hotter and more humid then the indoor air. If so, then the zone may be humidified with outdoor air by selecting an outdoor air fraction that will produce a supply air humidity ratio equal to the humidity ratio at the humidity setpoint and the indoor air temperature. However, if the indoor humidity is not available as a controllable parameter, then the method 300 proceeds directly to step 414.

At step 414, the temperature is monitored and when the zone reaches its maximum allowable temperature, the zone is switched from its maximum heat setpoint to regulated heating with a setpoint equal to the maximum allowable temperature.

At step 416, the time it takes to return to comfortable conditions is recalculated. The amount of time to return to comfortable conditions is dependent on the current state of the zone, the weather, and the HVAC system. In some embodiments, the time to cool-down that was calculated in step 406 is used.

At step 418, it is determined whether the time to switch from Disinfect Mode to return to comfortable conditions has been reached. If the switch time has not been reached, then the method 400 proceeds to step 416 and iterates until at step 418, it is determined that the switch time has been reached, at which point the method proceeds to step 420, where the heat is turned off and cooling of the zone is commenced. If the outdoor air is sufficiently cool, use economizer cooling.

At step 422, the mode is switched from Disinfect Mode, to either Green Mode, Health Mode, or control is released to the standard operating state of the BMS.

The method 400 ends at step 420.

Figure 5:
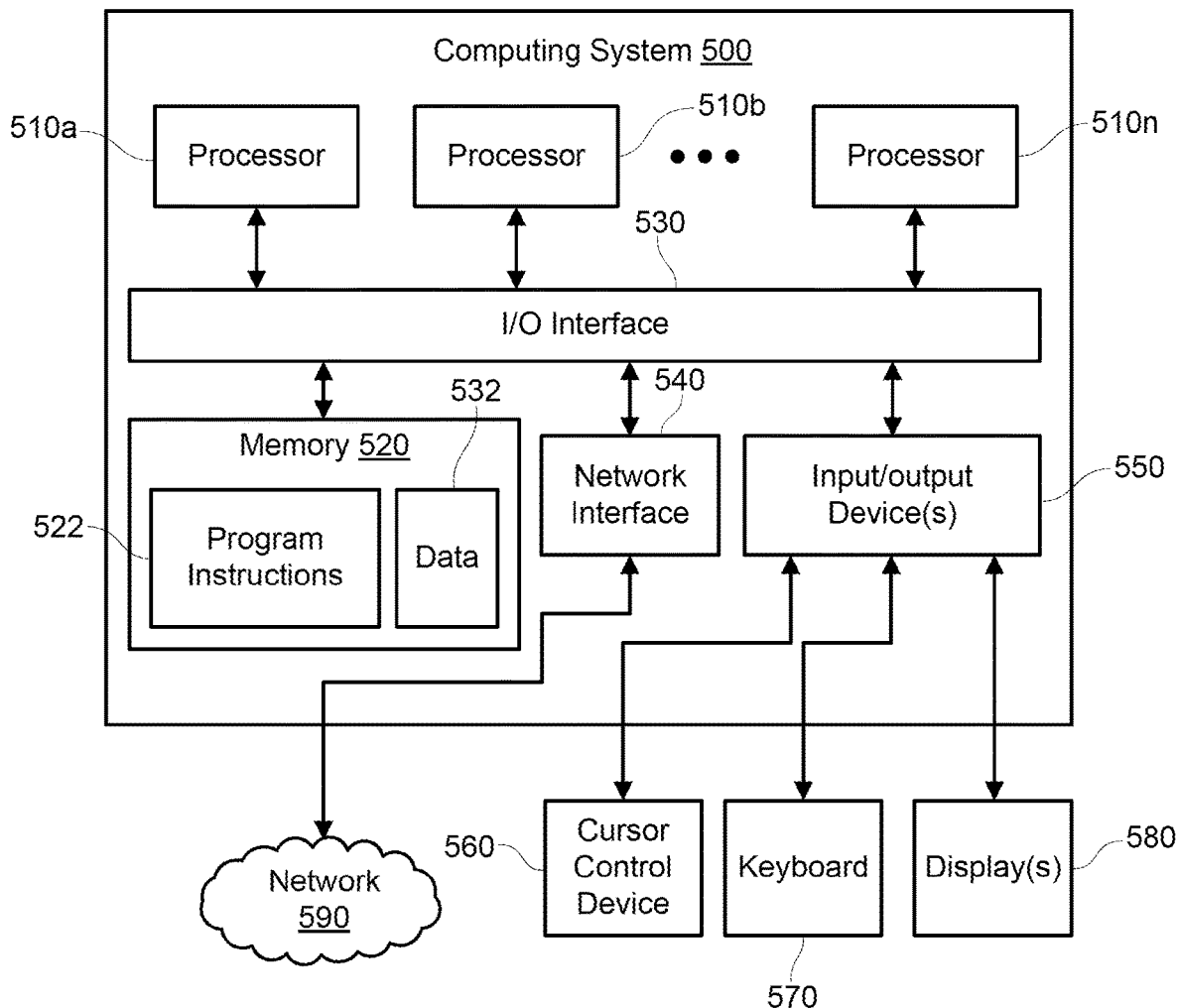
FIG. 5 is an exemplary diagram of a computer system for controlling the HVAC in a building to defend against pathogens, in accordance to one or more embodiments of the present invention.

FIG. 5 is an exemplary diagram of a computer system 500 for controlling the HVAC in a building to defend against pathogens in accordance to one or more embodiments of the present invention. The computer system 500 includes substantially similar structure comprising servers or electronic devices in the aforementioned embodiments.

Various embodiments of methods and system for controlling the HVAC in a building to defend against pathogens, as described herein, may be executed on one or more computer systems, which may interact with various other devices. One such computer system is computer system 500 illustrated by FIG. 5, which may in various embodiments implement any of the elements or functionality illustrated in FIGS. 1-4. In various embodiments, computer system 500 may be configured to implement methods described above. The computer system 500 may be used to implement any other system, device, element, functionality or method of the above-described embodiments. In the illustrated embodiments, computer system 500 may be configured to implement methods 200, 300, and 400 as processor-executable executable program instructions 522 (e.g., program instructions executable by processor(s) 510) in various embodiments.

In the illustrated embodiment, computer system 500 includes one or more processors 510a-510n coupled to a system memory 520 via an input/output (I/O) interface 530. Computer system 500 further includes a network interface 540 coupled to I/O interface 530, and one or more input/output devices 550, such as cursor control device 560, keyboard 570, and display(s) 580. In some embodiments, the keyboard 570 may be a touchscreen input device.

In various embodiments, a user interface may be generated and displayed on display 580. In some cases, it is contemplated that embodiments may be implemented using a single instance of computer system 500, while in other embodiments multiple such systems, or multiple nodes making up computer system 500, may be configured to host different portions or instances of various embodiments. For example, in one embodiment some elements may be implemented via one or more nodes of computer system 500 that are distinct from those nodes implementing other elements. In another example, multiple nodes may implement computer system 500 in a distributed manner.

In different embodiments, computer system 500 may be any of various types of devices, including, but not limited to, personal computer systems, mainframe computer systems, handheld computers, workstations, network computers, application servers, storage devices, a peripheral devices such as a switch, modem, router, or in general any type of computing or electronic device.

In various embodiments, computer system 500 may be a uniprocessor system including one processor 510, or a multiprocessor system including several processors 510 (e.g., two, four, eight, or another suitable number). Processors 510 may be any suitable processor capable of executing instructions. For example, in various embodiments processors 510 may be general-purpose or embedded processors implementing any of a variety of instruction set architectures (ISAs). In multiprocessor systems, each of processors 510 may commonly, but not necessarily, implement the same ISA.

System memory 520 may be configured to store program instructions 522 and/or data 532 accessible by processor 510. In various embodiments, system memory 520 may be implemented using any suitable memory technology, such as static random access memory (SRAM), synchronous dynamic RAM (SDRAM), nonvolatile/Flash-type memory, or any other type of memory. In the illustrated embodiment, program instructions and data implementing any of the elements of the embodiments described above may be stored within system memory 520. In other embodiments, program instructions and/or data may be received, sent or stored upon different types of computer-accessible media or on similar media separate from system memory 520 or computer system 500.

In one embodiment, I/O interface 530 may be configured to coordinate I/O traffic between processor 510, system memory 520, and any peripheral devices in the device, including network interface 540 or other peripheral interfaces, such as input/output devices 550. In some embodiments, I/O interface 530 may perform any necessary protocol, timing or other data transformations to convert data signals from one component (e.g., system memory 520) into a format suitable for use by another component (e.g., processor 510). In some embodiments, I/O interface 530 may include support for devices attached through various types of peripheral buses, such as a variant of the Peripheral Component Interconnect (PCI) bus standard or the Universal Serial Bus (USB) standard, for example. In some embodiments, the function of I/O interface 530 may be split into two or more separate components, such as a north bridge and a south bridge, for example. Also, in some embodiments some or all of the functionality of I/O interface 530, such as an interface to system memory 520, may be incorporated directly into processor 510.

Network interface 540 may be configured to allow data to be exchanged between computer system 500 and other devices attached to a network (e.g., network 590), such as one or more external systems or between nodes of computer system 500. In various embodiments, network 590 may include one or more networks including but not limited to Local Area Networks (LANs) (e.g., an Ethernet or corporate network), Wide Area Networks (WANs) (e.g., the Internet), wireless data networks, cellular networks, Wi-Fi, some other electronic data network, or some combination thereof. In various embodiments, network interface 540 may support communication via wired or wireless general data networks, such as any suitable type of Ethernet network, for example; via telecommunications/telephony networks such as analog voice networks or digital fiber communications networks; via storage area networks such as Fibre Channel SANs, or via any other suitable type of network and/or protocol.

Input/output devices 550 may, in some embodiments, include one or more display devices, keyboards, keypads, cameras, touchpads, touchscreens, scanning devices, voice or optical recognition devices, or any other devices suitable for entering or accessing data by one or more computer systems 500. Multiple input/output devices 550 may be present in computer system 500 or may be distributed on various nodes of computer system 500. In some embodiments, similar input/output devices may be separate from computer system 500 and may interact with one or more nodes of computer system 500 through a wired or wireless connection, such as over network interface 540.

In some embodiments, the illustrated computer system may implement any of the methods described above, such as the methods illustrated by the flowcharts of FIG. 2, FIG. 3, and FIG. 4. In other embodiments, different elements and data may be included.

Those skilled in the art will appreciate that computer system 500 is merely illustrative and is not intended to limit the scope of embodiments. In particular, the computer system and devices may include any combination of hardware or software that can perform the indicated functions of various embodiments, including computers, network devices, Internet appliances, smartphones, tablets, PDAs, wireless phones, pagers, and the like. Computer system 500 may also be connected to other devices that are not illustrated, or instead may operate as a stand-alone system. In addition, the functionality provided by the illustrated components may in some embodiments be combined in fewer components or distributed in additional components. Similarly, in some embodiments, the functionality of some of the illustrated components may not be provided and/or other additional functionality may be available.

Those skilled in the art will also appreciate that, while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 500 may be transmitted to computer system 500 via transmission media or signals such as electrical, electromagnetic, or digital signals, conveyed via a communication medium such as a network and/or a wireless link. Various embodiments may further include receiving, sending or storing instructions and/or data implemented in accordance with the foregoing description upon a computer-accessible medium or via a communication medium. In general, a computer-accessible medium may include a storage medium or memory medium such as magnetic or optical media, e.g., disk or DVD/CD-ROM, volatile or non-volatile media such as RAM (e.g., SDRAM, DDR, RDRAM, SRAM, and the like), ROM, and the like.

The methods described herein may be implemented in software, hardware, or a combination thereof, in different embodiments. In addition, the order of methods may be changed, and various elements may be added, reordered, combined, omitted or otherwise modified. All examples described herein are presented in a non-limiting manner. Various modifications and changes may be made as would be obvious to a person skilled in the art having benefit of this disclosure. Realizations in accordance with embodiments have been described in the context of particular embodiments. These embodiments are meant to be illustrative and not limiting. Many variations, modifications, additions, and improvements are possible. Accordingly, plural instances may be provided for components described herein as a single instance. Boundaries between various components, operations and data stores are somewhat arbitrary, and particular operations are illustrated in the context of specific illustrative configurations. Other allocations of functionality are envisioned and may fall within the scope of claims that follow. Finally, structures and functionality presented as discrete components in the example configurations may be implemented as a combined structure or component. These and other variations, modifications, additions, and improvements may fall within the scope of embodiments as defined herein.

The invention claimed is:

1. A computer implemented method for controlling a heating, ventilation, and air conditioning (HVAC) system in a building to defend against pathogens, comprising:
estimating a latent load of air in a zone being disinfected;
selecting at least one set of one or more control variables from a plurality of control variables to improve a metric;
adjusting the metric for the at least one set of one or more control variables; and
changing a setpoint of each control variable in the at least one set of one or more control variables when the metric has converged.

2. The method of claim 1, wherein the at least one set of one or more control variables includes one or more of a supply airflow rate, an outdoor airflow rate, or an indoor temperature.

3. The method of claim 1, wherein the metric is one or more of energy consumption, pathogen loss rate, or a probability of infection.

4. The method of claim 1, wherein the plurality of control variables comprises multiple sets of control variables, and wherein selecting the at least one set of one or more control variables comprises selecting all sets of the multiple sets of control variables.

5. The method of claim 1,
wherein the at least one set of one or more control variables includes indoor humidity.

6. The method of claim 1, wherein adjusting comprises one of optimizing the metric or regulating the metric to use a least amount of power consumption while conforming to comfort constraints.

7. The method of claim 1, further comprising:
determining that all occupants of the zone being disinfected have evacuated the zone;
initiating a disinfect mode of the HVAC system, comprising determining a maximum temperature threshold for the zone that is being disinfected;
determining a switch time that the disinfect mode must cease in order to cool down the zone in order to reach comfortable conditions before occupants return to the zone;
maximizing a heat output of the HVAC system to the zone that is being disinfected; and
switching to a cool down phase when the determined time to cool down the zone has been reached.

8. The method of claim 7, wherein a latest time that the disinfect mode must cease is a predetermined time.

9. The method of claim 7, wherein maximizing the heat output comprises setting the setpoint of the heat output to the maximum temperature threshold.

10. The method of claim 7, further comprising:
determining the zone has reached the maximum temperature threshold; and
switching the zone from maximum heating to regulated heating with a setpoint equal to the maximum temperature threshold.

11. The method of claim 7, wherein maximizing the heat output comprises:
determining the outdoor air is hotter and less humid than the indoor air; and
using the outdoor air to heat the zone.

12. The method of claim 7, further comprising setting a humidity setpoint to a maximum value.

13. The method of claim 12, further comprising:
determining the outdoor air is hotter and more humid than the indoor air; and
humidifying the zone with outdoor air by selecting an outdoor air fraction that produces a supply air humidity ratio equal to the humidity ratio at the humidity setpoint and an indoor air temperature.

14. The method of claim 1, wherein the method is triggered by an informatics system indicating that a health metric has crossed a level that indicates that building occupants may be infected with a pathogen.

15. A system for controlling a heating, ventilation, and air conditioning (HVAC) system in a building to defend against pathogens, comprising:
a pathogen defense system comprising:
a) at least one processor;
b) at least one input device; and
c) at least one storage device storing processor-executable program instructions which, when executed by the at least one processor, perform a method comprising:
selecting at least one set of one or more control variables from a plurality of control variables to improve a metric;
adjusting the metric for the set of one or more control variables; and
changing a setpoint of each control variable in the set of one or more control variables when the metric has converged.

16. The system of claim 15, wherein the at least one set of one or more control variables includes one or more of a supply airflow rate, an outdoor airflow rate, or an indoor temperature.

17. The system of claim 15, wherein the plurality of control variables comprises multiple set of control variables, and wherein the at least one set of one or more control variables comprises all sets of multiple set of one or more control variables.

18. The system of claim 15, wherein the metric is one or more of energy consumption, pathogen loss rate, or a probability of infection.

19. The system of claim 15, wherein adjusting comprises optimizing the metric to use a least amount of power consumption while conforming to comfort constraints.

20. The system of claim 15, further comprising:
determining that all occupants of a zone being disinfected have evacuated the zone; and
initiating a disinfect mode of the pathogen defense system.

21. The system of claim 20, wherein initiating the disinfect mode comprises:

determining a maximum allowable temperature threshold for the zone that is being disinfected;

determining a switch time that the disinfect mode must cease in order to cool-down the zone in order to reach comfortable conditions before occupants return to the zone;

maximizing a heat output of the HVAC system to the zone that is being disinfected; and turning off disinfect mode when the determined time to cool-down the zone has been reached.

22. A computer implemented method for controlling an HVAC system in a building to defend against pathogens, comprising:

estimating a latent load of air in a zone being disinfected;

selecting a set of one or more control variables from a plurality of control variables to optimize a metric;

adjusting the metric for the set of one or more control variables based on the estimated latent load; and displaying values for the set of one or more control variables for which the metric is optimized.

* * * * *